(12) United States Patent
Von Schuckmann

(10) Patent No.: US 8,701,660 B2
(45) Date of Patent: *Apr. 22, 2014

(54) INHALER FOR POWDERY SUBSTANCES, IN PARTICULAR MEDICINAL SUBSTANCES

(75) Inventor: Alfred Von Schuckmann, Kevelaer (DE)

(73) Assignee: Siegfried Generics International, Zofingen (CH)

( * ) Notice: Subject to any disclaimer, the term of this patent is extended or adjusted under 35 U.S.C. 154(b) by 1347 days.

This patent is subject to a terminal disclaimer.

(21) Appl. No.: 12/062,225

(22) Filed: Apr. 3, 2008

(65) Prior Publication Data

US 2008/0223365 A1  Sep. 18, 2008

Related U.S. Application Data

(62) Division of application No. 11/660,887, filed as application No. PCT/EP2005/054094 on Aug. 19, 2005, now Pat. No. 8,327,842.

(30) Foreign Application Priority Data

Aug. 27, 2004  (DE) .................. 10 2004 041 524

(51) Int. Cl.
  *A61M 16/00* (2006.01)
  *A61M 15/00* (2006.01)
  *B05D 7/14* (2006.01)
  *B65D 83/06* (2006.01)

(52) U.S. Cl.
  USPC ............. 128/203.15; 128/203.12; 128/203.13

(58) Field of Classification Search
  CPC .................. A61M 2202/064; A61M 2202/06; A61M 2202/062; A61M 15/0028; A61M 15/00; A61M 15/0091; A61M 2015/00; A61M 2015/0061; A61M 2015/0025; A61M 2015/0021

USPC ............. 128/203.15, 203.12, 203.19, 203.21, 128/200.11, 200.12, 200.14, 200.21, 128/200.23, 200.24, 203.13, 203.14, 128/203.16, 203.22, 203.23; 222/630, 636, 222/366, 344, 361, 367, 425, 452
  See application file for complete search history.

(56) References Cited

U.S. PATENT DOCUMENTS 2,029,835 A  2/1936  Reichle
(Continued)

FOREIGN PATENT DOCUMENTS

DE  10047722 A1  4/2002
(Continued)

OTHER PUBLICATIONS

International Search Report.

*Primary Examiner* — Justine Yu
*Assistant Examiner* — Colin W Stuart
(74) *Attorney, Agent, or Firm* — McDonnell Boehnen Hulbert & Berghoff LLP

(57) ABSTRACT

An inhaler for powdered, particularly medicinal substances, is formed with a suction air duct that extends to a mouthpiece, a reservoir for the substance, and an at least linearly movable dosing chamber for separating a specific amount of the substance from the reservoir and placing the amount into a transfer position from where it is transferred to a suction air flow. In order to charge the dosing chamber by separating a specific amount of substance from the reservoir, the dosing chamber can be rotationally moved in a superimposed fashion while being arranged eccentric to a corresponding axis of rotation. A closure slide element closes off the dosing chamber in the transfer position. When suction is applied, the closure slide element moves relative to the dipping plunger into a dose-release position, whereupon the dose of the powdered substance is transferred to the suction air stream formed in the suction air duct.

15 Claims, 6 Drawing Sheets

(56) References Cited

U.S. PATENT DOCUMENTS

| | | | |
|---|---|---|---|
| 4,095,596 A * | 6/1978 | Grayson | 128/203.21 |
| 4,117,946 A * | 10/1978 | Kessler | 215/321 |
| 5,239,992 A * | 8/1993 | Bougamont et al. | 128/203.15 |
| 5,429,122 A | 7/1995 | Zanen et al. | |
| 5,435,301 A | 7/1995 | Herold et al. | |
| 5,505,196 A | 4/1996 | Herold et al. | |
| 5,524,613 A | 6/1996 | Haber et al. | |
| 5,628,307 A * | 5/1997 | Clark et al. | 128/203.15 |
| 6,119,688 A * | 9/2000 | Whaley et al. | 128/203.15 |
| 6,371,111 B1 | 4/2002 | Ohki et al. | |
| 6,488,648 B1 | 12/2002 | Matsugi et al. | |
| 6,814,072 B1 | 11/2004 | Seppälä | |
| 2003/0136405 A1 * | 7/2003 | Goede et al. | 128/203.12 |
| 2004/0035421 A1 | 2/2004 | Schuckmann | |
| 2004/0187868 A1 | 9/2004 | Hochrainer et al. | |
| 2007/0289593 A1 * | 12/2007 | von Schuckmann | 128/203.15 |
| 2010/0300441 A1 * | 12/2010 | Von Schuckmann et al. | 128/203.15 |
| 2010/0309020 A1 * | 12/2010 | Von Schuckmann et al. | 340/870.01 |

FOREIGN PATENT DOCUMENTS

| | | |
|---|---|---|
| DE | 10106788 A1 | 8/2002 |
| DE | 10144572 A1 | 3/2003 |
| RU | 2138303 C1 | 9/1999 |
| WO | 0064518 A1 | 11/2000 |
| WO | 0226299 A1 | 4/2002 |

\* cited by examiner

FIG 6
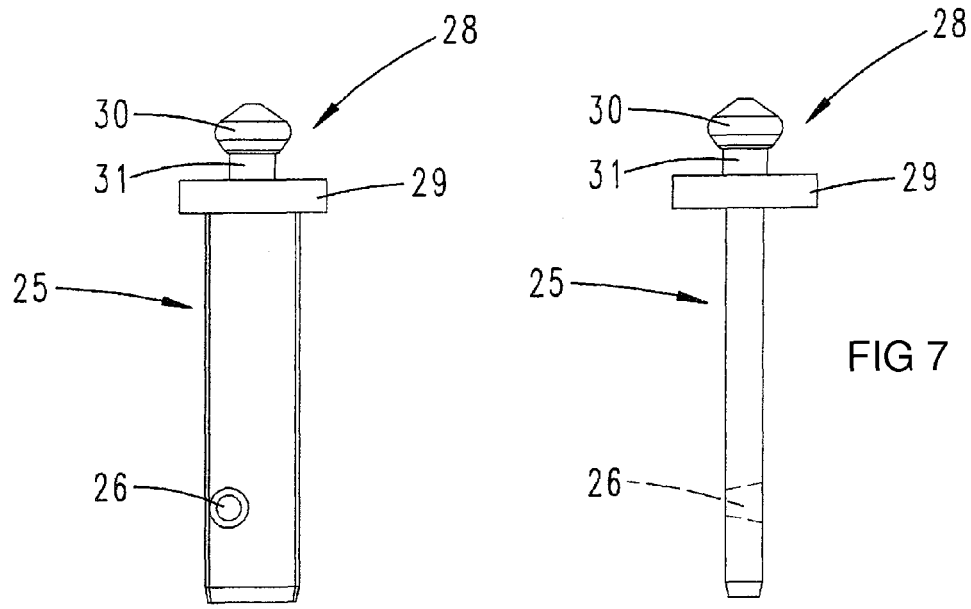
FIG 7
FIG 8
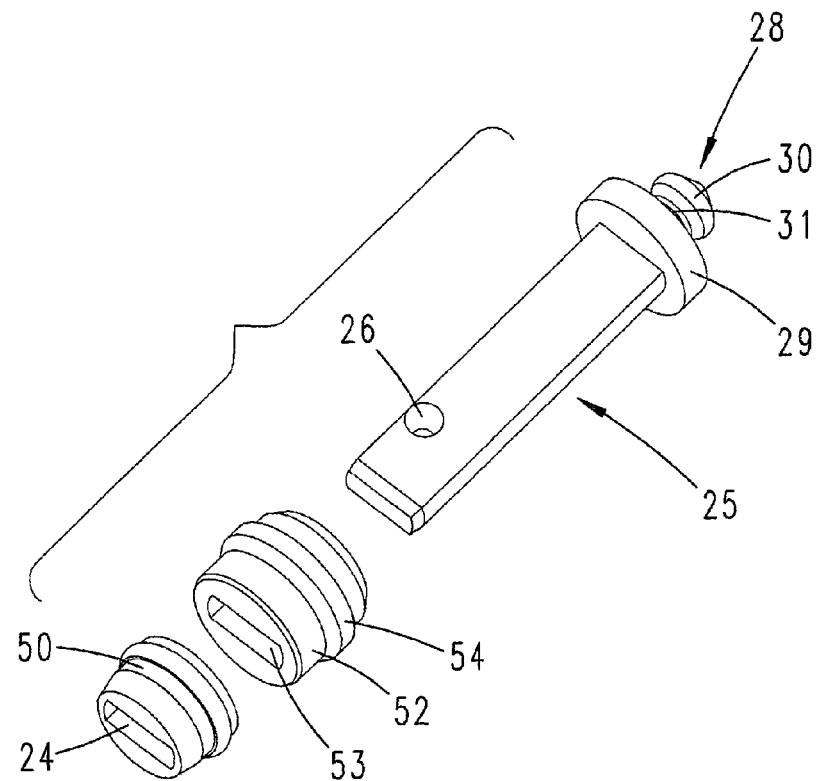

INHALER FOR POWDERY SUBSTANCES, IN PARTICULAR MEDICINAL SUBSTANCES

CROSS-REFERENCE TO RELATED APPLICATION

This application is a divisional of application Ser. No. 11/660,887, filed Feb. 23, 2007; which was a §371 national stage application of international application PCT/EP05/054094, filed Aug. 19, 2005; this application also claims the priority, under 35 U.S.C. §119, of German patent application No. DE 10 2004 041 524.2, filed Aug. 27, 2004; the prior applications are herewith incorporated by reference in their entirety.

BACKGROUND OF THE INVENTION

Field of the Invention

The invention relates to an inhaler for powdered, particularly medicinal, substances, according to the preamble of the main claim.

An inhaler of this general type is known from U.S. Pat. No. 5,429,122. There, the removal of a push-on closure cap results in the upward movement of the annular dosing chamber under spring force, bringing the dosing chamber into the region of a suction air stream. If the suction is not rapid and strong, small amounts of the substance being inhaled can fall downward in the air stream channel, despite suitably rapid lifting of the dosing chamber by the aforesaid spring force.

BRIEF SUMMARY OF THE INVENTION

It is an object of the invention to provide an inhaler for powdery, in particular medicinal, substances, which overcomes the above-mentioned disadvantages of the heretofore-known devices and methods of this general type and which is refined so as to provide advantages, in particular advantages relating to the charged dosing chamber.

With the foregoing and other objects in view there is provided, in accordance with the invention, an inhaler for powdery substances, comprising:

a mouthpiece and a suction air channel leading to the mouthpiece;

a storage chamber for storing therein the powdery substance;

a movable dosing chamber for apportioning a specific amount of substance from the storage chamber and moving an amount of substance into a ready position (i.e., a ready-to-empty transfer position) for transferring the amount of substance to a suction air stream;

a closure slide element disposed to close off the dosing chamber in the ready position, and movable relative to a dipping plunger into a dose-release position upon application of a suction underpressure.

In other words, according to the invention, the dosing chamber is moved into a closed delivery-ready transfer position, wherewith the dosing chamber remains closed until opened by a sufficiently strong suction air stream. The dosing chamber is moved in a helical path into the transfer position where it can deliver its contents to the suction air stream, to effect the inhalation when and if the patient provides a sufficiently strong suction air stream. This helps to avoid undesirable unmixing of the substance being delivered, which substance usually is comprised of a plurality of components.

According to the invention, the dosing chamber is formed in a dipping plunger which has a flattish shape, i.e., a flat-part plunger slide.

The flat shape of the dipping plunger enables good positioning of the axially slidable closure member in the closing position (enables effective closing by the closure member), while allowing sufficient slidability.

It is advantageous to have the dosing chamber in the form of a transverse bore in the flat-part dipping plunger.

In this connection it has been found to be particularly advantageous if the dipping plunger is movable by means which are dependent upon manipulations of the closure cap, so that in the course of carrying out the customary manipulations for closing and opening of the device, the rotation of the closure cap will also cause charging of the dosing chamber and a helical movement of the dosing chamber into the closed ready-to-release transfer position.

It is particularly effective if the transverse bore comprising the dosing chamber has a (frusto)conical shape.

The cross sectional dimensions of the flattish piece of which the dipping plunger is comprised have a ratio in the range of approximately 1:2 to 1:5. The flattish cross section of the dipping plunger favors the breaking up and loosening of the subject substance stored in the central region of the storage chamber, and promotes the progression of the dipping plunger into the mass of powder and the complete charging (of the dosing chamber).

The axially slidable closure member is linearly movable relative to the dipping plunger; the flattish dipping plunger throughgoingly extends through the slidable closure member in rotationally rigid fashion but in a manner such that the friction between the two components is low.

The end of the dosing chamber having the larger open diameter is associated with an air passage of smaller diameter than the end of the dosing chamber, and the end of the dosing chamber having the smaller open diameter is associated with a second air passage of larger diameter than the smaller end. This tends to provide a larger underpressure on the end with the larger open diameter.

It is further proposed according to the invention that the air passages are formed in a cup-shaped rotary piece which guides the dipping plunger, and the air passages are in fluid communication with air inlets in the shell (lateral wall) of the mouthpiece. The air inlets are located in the shell of the mouthpiece at locations chosen such that neither the patient's lips nor the hand by which the patient generally surroundingly holds the generally stick-shaped device will occlude the air inlets.

A plurality of air inlets may be provided which are disposed at mutual distances, in order to further minimize the risk of air inlet occlusion.

To promote good distribution of the powdered substance in the suction air stream, the air passages may be axially displaced with respect to the air inlets, which may be closer to the mouthpiece. The effect of this is that, upon opening of the device, the flow path will be U-shaped.

It has further been found advantageous if the generally cup-shaped bottom of the rotary part forms the cover for the storage chamber, and the center of the cup-shaped bottom has a guide opening for the dipping plunger. The cup-shaped bottom thus has a dual function—serving as a direct or indirect cover, and serving as a guide for the dipping plunger.

It is also advantageous if the dipping plunger, which is to some extent tapered toward its dipping end in the manner of the blade of a screwdriver, is rotationally connected to the rotary part by means of radial lobes. The blade-like tip region provides a rotational breaking up and loosening effect, and also facilitates insertion of the dipping plunger into the powder mass; and the radial lobes help to support the dipping plunger with respect to the rotary part and to assist in maintaining the positioning of the air passages with respect to the dosing chamber.

Simple means are provided to facilitate the necessary linear relative movement of the dipping plunger and the rotary part, which means may comprise axial guide grooves in the cup-shaped wall of the cup-shaped rotary part, in which grooves the aforethe lobes are guided.

According to a further feature of this solution, a stroke-limiting detent for the dipping plunger is provided, which detent, via its base wall section, defines the ready-to-empty position (transfer location) of the dosing chamber.

The positioning of the dipping plunger based on manipulation of the closure cap is aided by a feature according to which a "docking point" (docking position structure) is provided which is disposed at or near the mouthpiece end which docking position structure has latching means whereby the dipping plunger and the closure cap can interengage, which latching means can be disengaged by application of force tending to pull the plunger and cap mutually apart. When the inhaler is re-closed, the dipping plunger and closure cap are mutually re-engaged by mutual thrust, giving rise to a "re-docking."

According to an important refinement, the rotary piece has a rotor, and a corresponding stator, the rotor and stator cooperating to provide a shoveling effect to deliver (material) to the dosing chamber when the rotary piece is "rotated back." With this arrangement, from one instance to another of filling of the dosing chamber the amount of the powder charged, and its density, remains constant. Also, the shoveling action tends to loosen the nearby powder mass, thus tending to prevent caking and lumping of the powder particles. The phrase "rotated back" refers to the effect of unscrewing of the closure cap, which is accompanied by charging of the dosing chamber. The shoveling mechanism is comprised of rotor blades borne on a cantilever structure wherewith they extend from a ring-shaped disc member at the bottom of the rotary part.

It is also proposed that the closure cap is in the form of a screw cap and cooperates with the mouthpiece via rotational (which is to say non-rotation) engagement means. The latter have a deep notch or forked structure and are configured so as to disengage when the cap is ultimately unscrewed.

To further improve the distribution of the powdered substance or the apportioned amount of substance in the suction air, the so-called dispersing region, downstream of the transfer region in the direction of flow, is further formed in an advantageous way to the extent that the suction air channel has a radially outward deflection above the dosing chamber. Accordingly, before the amount of substance transferred to the suction air stream leaves, it also undergoes a deflection, this radially outward deflection also leading into an outlet portion in the region of the mouthpiece that is similar to an annular space. Correspondingly, the substance leaves in the form of a circular ring if the mouthpiece is viewed looking down on top of it. It is also proposed that the plunger slide itself forms part of the flow deflection, for instance in particular such that, in an end region facing away from the flat part having the dosing chamber and correspondingly facing toward the mouthpiece, it takes the form of a disk of a circularly round outline, which offers the radially outward deflection of the suction air channel in the transfer position.

Other features which are considered as characteristic for the invention are set forth in the appended claims.

Although the invention is illustrated and described herein as embodied in inhaler for powdered, particularly medicinal substances, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

The invention is explained in more detail below with reference to the accompanying drawings, which merely represent an exemplary embodiment and in which:

BRIEF DESCRIPTION OF THE SEVERAL VIEWS OF THE DRAWING

FIG. 6 shows the plunger slide having the dosing chamber on its own in elevation;

FIG. 7 shows the side view of this; and

FIG. 8 shows the plunger slide in a perspective representation, with a closure plunger that can be associated with it and with a sealing bush.

DETAILED DESCRIPTION OF THE INVENTION

Figure 1:
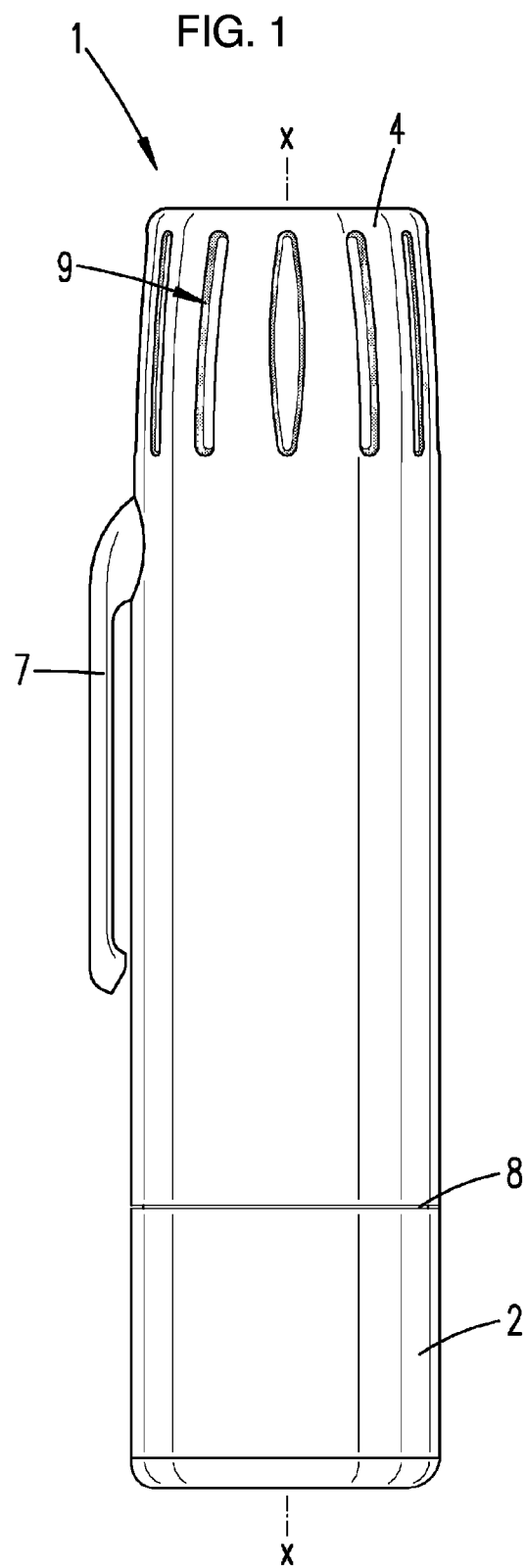
FIG. 1 shows the inhaler according to the invention in side view, enlarged, in the basic position with the cap closed.

Referring now to the figures of the drawing in detail, there is shown and described an inhaler 1, which is realized as a conveniently portable pocket device in the form of a short stick, with a shape-determining stepped cylindrical housing 2.

The cylindrical housing which is like a small tube passes at the top end of the inhaler 1 into an attached mouthpiece 3 which is flattened appropriately for a mouth and can be protectively engaged over by means of a cup-shaped closure cap 4. The latter is realized as a screw cap, for which purpose an internal thread 5 associated with it engages in a corresponding external thread 6 on the lateral wall of the housing 2. In the region where the mouthpiece 3 is attached/a clip 7 is integrally formed on the outer sleeve wall of the closure cap 4.

At the bottom end, the end edge of the cup-shaped closure cap 4 butts with a stop-limiting and sealing effect against an annular shoulder 8, which is achieved on account of the aforementioned step of the cylindrical housing 2.

The closure cap 4 serves at the same time as an actuating handle 9 for delivering a powdered substance in reproducible portions 10', for which purpose the axial screw stroke of the engagement of the threads 5/6 is used. The substance 10 is accommodated in a storage chamber 11 of the housing 2 in an optionally refillable manner. The dosing device, transporting in each case a portion 10' to a transfer point U lying outside the storage chamber 11, is designated as a whole by D.

With respect to the material that can be dosed, it is a medical, powdered substance 10. For example, basic substances capable of being transported by suction stream, such as lactose, may act as a carrier for micronized fine particles of medicament sticking to the surface.

Provided downstream of the dosing device D is a so-called dispersing region, in which the user produces a suction air stream S. This completely carries away the exactly apportioned amount 10' of the substance 10 at the transfer point U. The suction air channel leading to the mouthpiece 3 is provided with the reference numeral 12.

The lower termination of the storage chamber 11 is formed by a cup-shaped pressure-exerting base 13, which is under spring loading in the direction of the mouthpiece 3 by means of a compression spring 14. The compression spring 14 is supported by the bottom end turn on a base cap 15 closing the housing 2 there. The base cap is in latching engagement with the portion of the housing 2, which is here of larger cross-section, a corresponding latching collar 16 of the base cap 15 engaging in a matching annular groove of the housing 2.

The top end turn of the prestressed compression spring 14 acts in loading manner on an inner shoulder 17 of a hollow piston 18 of the piston-shaped device 13/18. As can be gathered from the illustrations, the stepped cup-shaped pressure-exerting base 13 is connected in a latching manner to the inner shoulder 17 of the hollow piston 18.

The cup edge of the pressure-exerting base 13 provides an annular lip 19, which on account of its rubberelastic material wipes off the wall of the storage chamber 21 without any substance being lost.

A hollow standing spigot 20 extends centrally from the base cap 15. Together with the hollow piston 18 surrounding it at a spacing, the standing spigot forms a spring chamber 21 for the compression spring 14.

At the mouthpiece end, the storage chamber 11 terminates with a cup-shaped rotary part 22, which forms by its cup base the top 23 of the storage chamber 11 engaging over the housing 2.

A guiding opening 24 is left at the center of the top 23. This indirectly or directly formed guiding opening 24 receives a plunger slide 25, as the key component of the dosing device D. As a result of being appropriately configured, the plunger slide acts as a moving dosing chamber 26 for the portion 10' to be lifted out, the movement of the plunger slide 25 taking place linearly in the longitudinal center axis x-x of the substantially rotationally symmetrically configured inhaler 1, overlaid by a rotational movement carried out about this longitudinal center axis x-x. The plunger slide 25 is fashioned substantially as a flat part with an elongate rectangular cross-section. The length ratio of the narrow side to the wide side in the exemplary embodiment represented is approximately 1:3.

At the end remote from the mouthpiece 3, the plunger slide 25 forms a point similar to a screwdriver blade. The two mirror-symmetrical oblique flanks extend here from the respective wide sides of the plunger slide 25. The free end, provided with the oblique flanks, is blunted.

On account of the co-rotation of the plunger slide 25, the cross-sectional configuration of the plunger slide 25 and the pointing of the free end region have a loosening effect in the central region with respect to the mass of powdered substance 10.

The stroke of the dosing chamber 26, moving in a linear manner with superposed rotational movement, makes allowance in both end positions of the plunger slide 25 for the cross-section of the guiding opening 24 to be kept closed with a doctor-blade or wiping-off effect, filling the dosing chamber, over the length of the opening 24.

The end of the closure cap 4 for the mouthpiece forms a docking point 28 between plunger slide 25 and closure cap 4 that unlatches when overloaded. The latching means on the closure cap is in this case a ring of hooks capable of resilient deflection. The corresponding end of the plunger slide 25 is fashioned in a rotationally symmetrical manner in cross-section, a disk-shaped radial collar 29 also emerging in the transitional region from the flat part portion to the cylindrical end portion. With an axial spacing in relation to this radial collar 29, the end region of the plunger slide 25 that is facing away from the flat part fashions a latching head 30. Between the latching head and the radial collar 29 there is formed a narrow waist-like annular groove 31. Inwardly directed lugs 32 of the resilient tongues of the ring of hooks engage in the annular groove. The latching head 30 can be overcome in both directions by the lugs 32.

The lugs 29, or their resilient tongues, are realized on a small tube 33 which protrudes into a central mouthpiece opening 3' and extends from the inner side of the top of the closure cap 4, at which it is rooted.

The mouthpiece 3 acts via a lateral wall 34 in an anchoring manner on the neck of the housing 2. With reference to the illustrations, this anchorage is formed underneath the top 23 of the rotary part in the form of a latching point 35 between the two parts 2, 3. It may be an irreversible latching point 35. In addition, the top 23 of the rotary part 22 is engaged over in a supported manner by an annular shoulder 36 of the lateral wall 34.

The central opening 3' of the mouthpiece 3 is formed in the region of a cup-shaped dispersing part 37, disposed substantially in an inverted position. This is accomplished by passing centrally through the base 38 of the dispersing part. The dispersing part 37, opening in the direction of the rotary part 22, has a cup wall 39, with an outside diameter which corresponds to the outside diameter of the cup wall 40 of the rotary part 22. The cup-shaped rotary part 22 and the cup-shaped dispersing part 37 face each other with their openings, the dispersing part 37 being supported with its free annular edge on the associated annular edge of the cup wall 40 of the rotary part.

Both cup walls 39 and 40 are spaced radially inward in relation to the inner wall of the lateral wall 34. Correspondingly, an annular space 41 is respectively obtained around the rotary part 22 and around the dispersing part 37.

The inside diameter of the cup wall 39 of the dispersing part 37 is adapted to the outside diameter of the disk-like radial collar 29 of the plunger slide 25. The latter correspondingly undergoes guidance in a linear direction in the cup-like dispersing part 37.

Respectively toward their open end regions, the cup spaces both of the rotary part 22 and of the dispersing part 37 widen radially outward, with the material of the respective cup walls 39 and 40 being reduced. As a result of this configuration, a radially widened overflow region 42 is obtained.

Spaced away from the cup base 38 of the dispersing part 37 by approximately the material thickness of the radial collar 29 of the plunger slide 25, radial passages 43 are provided in the cup wall 39, for connecting the space inside the cup with the peripheral annular space 41. As shown, two diametrically opposed passages 43 may be provided.

Alternatively, one peripheral passage, interrupted by supporting webs, may also be provided. The annular discharge space 44, surrounding the cup base 38 of the dispersing part 37 is separated from the annular space 41 extending approximately as an axial extension by a sealing collar 45, which protrudes radially outward on the cup wall 39, which sealing collar 45 is supported on the inside of the lateral wall 34. As a result of this configuration, a defined deflection of the suction air channel 12 is achieved, from the central axial alignment radially outward into the substantially axially aligned annular outlet space 44.

The axial lengths of the rotary part 22 and the dispersing part 37 in the region of their cup walls 39 and 40 are chosen such that the powder-drawing plunging stroke of the plunger slide 25 out of a filling plane in the storage chamber 11 to the transfer point U above the top 23 is ensured.

The defined ready-to-empty position of the dosing chamber 26 is obtained by an extension limiting stop of the plunger slide 25 in the region of its radial collar 29 against the cup base 38 of the dispersing part 37.

The dosing chamber 26 is realized as a transverse bore running substantially perpendicularly in relation to the longitudinal center axis x-x.

Figure 2:
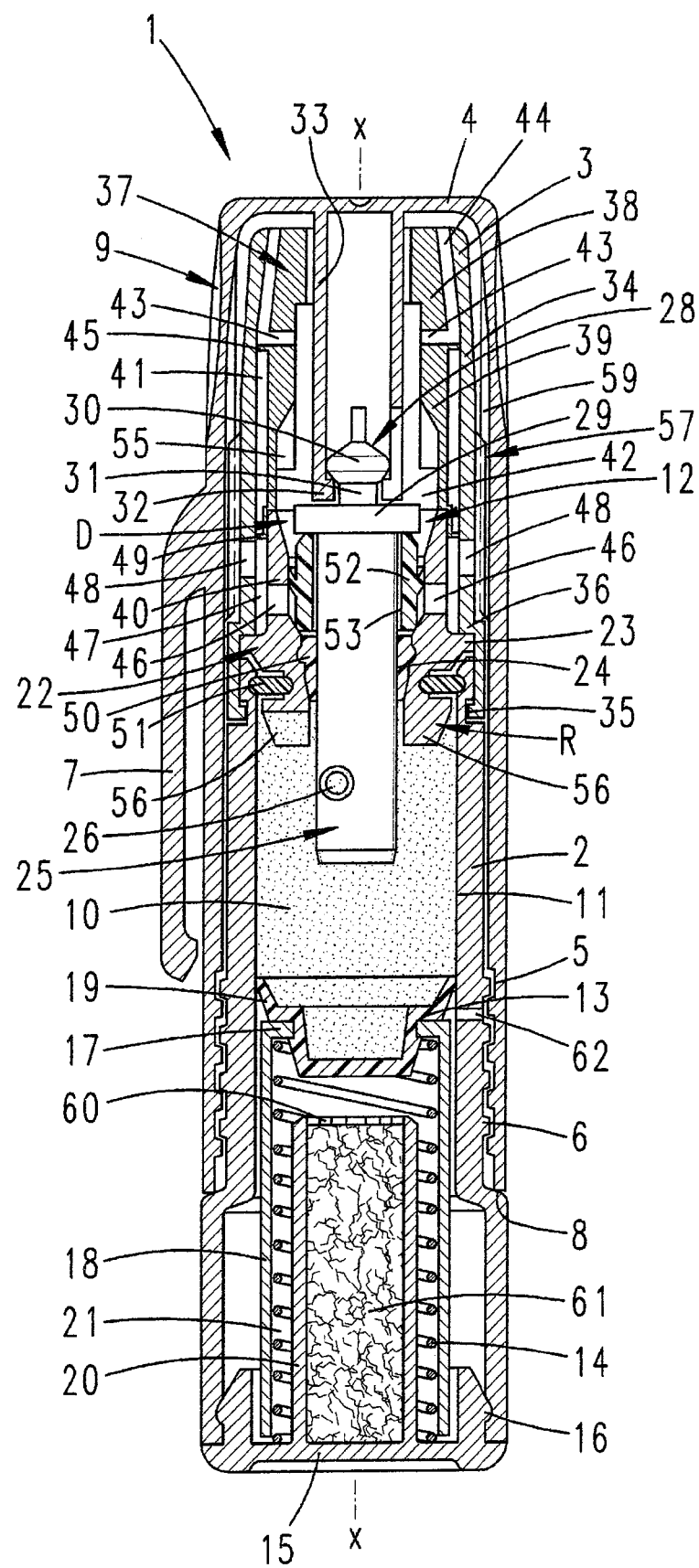
FIG. 2 shows the vertical section of this.
Figure 3:
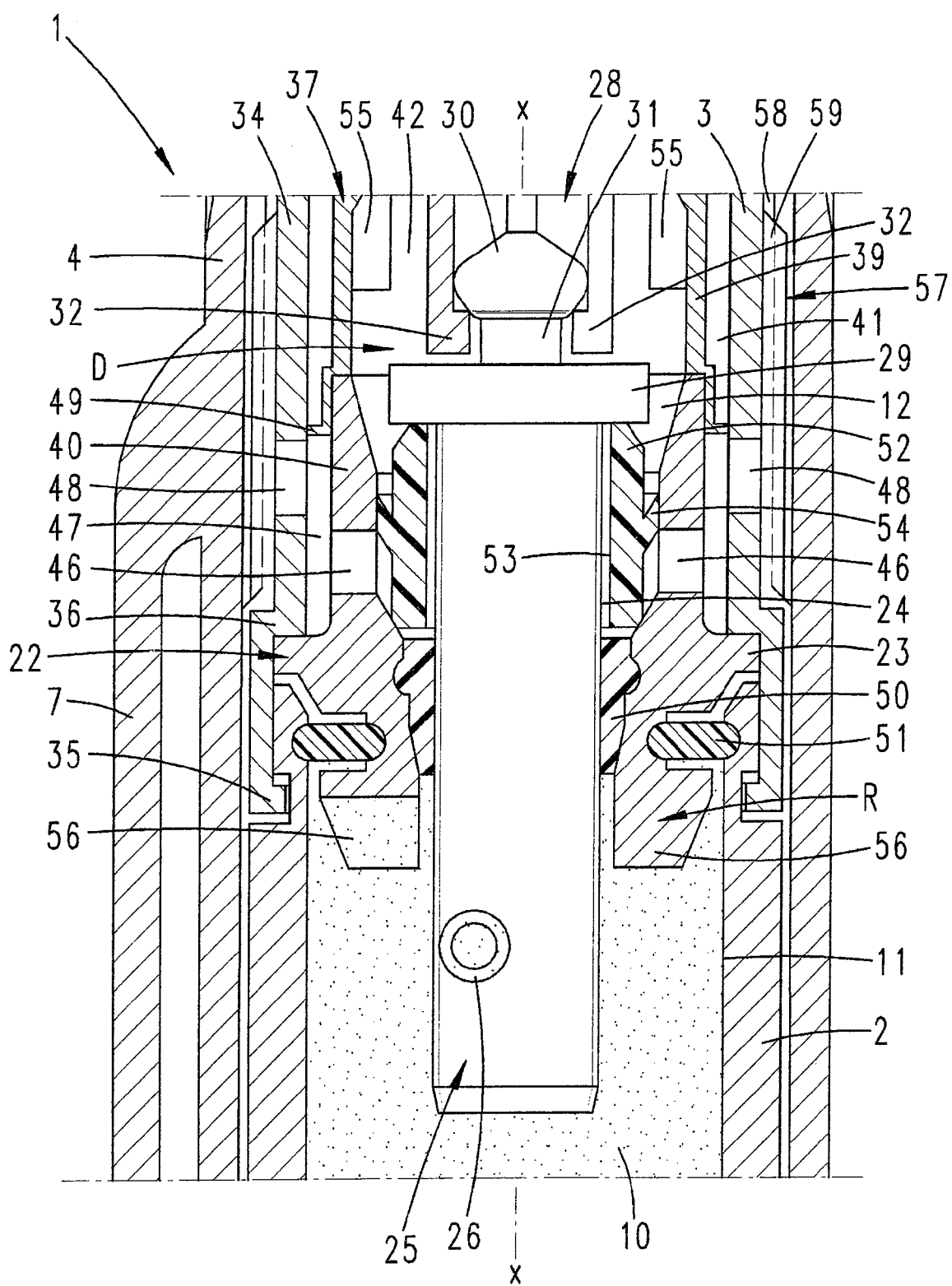
FIG. 3 shows an enlargement taken from FIG. 2, for the region of a dosing device.

This longitudinal center axis x-x at the same time forms the axis of rotation. The dosing chamber 26 is eccentrically disposed with respect to this axis of rotation, so furthermore passes through the wide sides of the plunger slide 25 fashioned as a flat part. As can be gathered in particular from the illustration in FIG. 2, the dosing chamber 26 is disposed such that it is associated with a side edge of the wide surface, at a spacing from the free end of the plunger slide 25.

Figure 4:
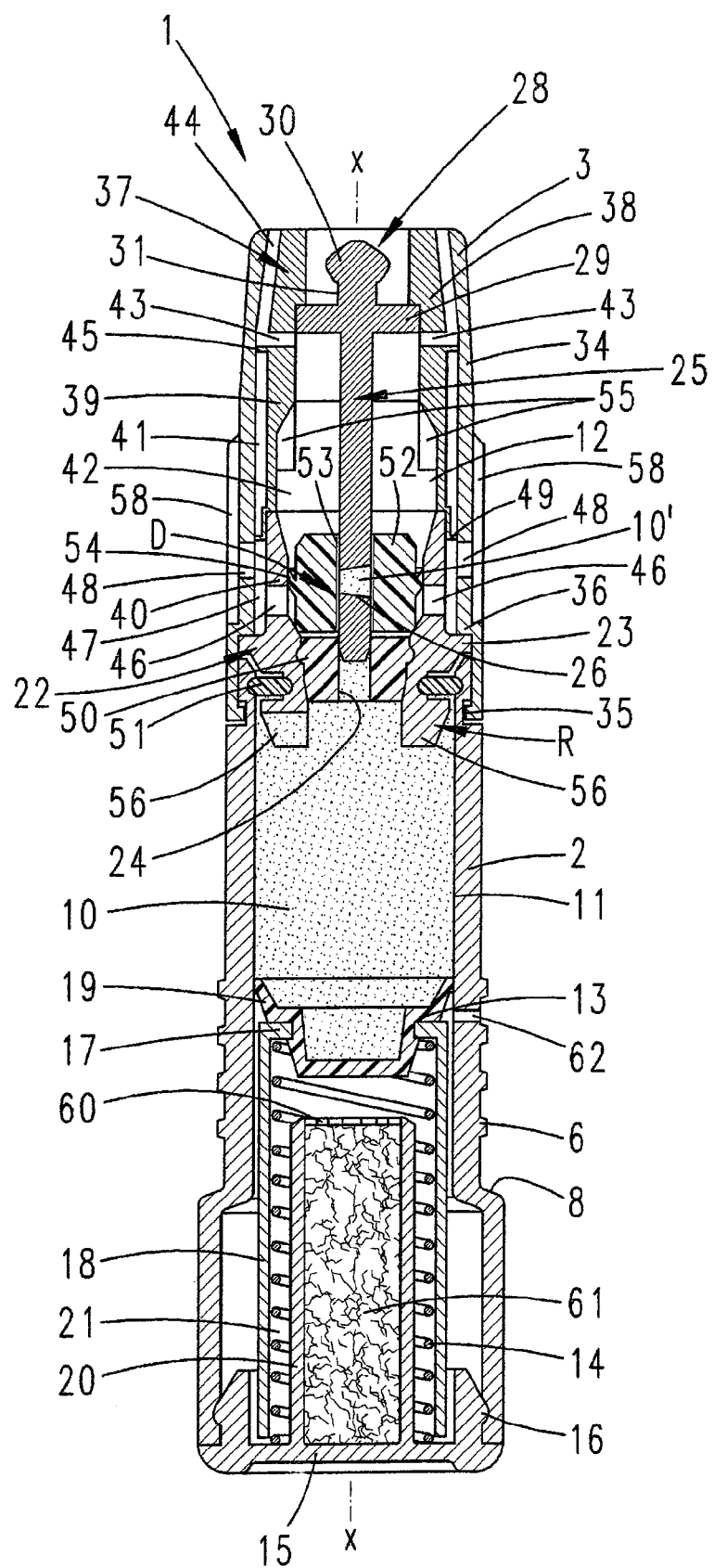
FIG. 4 shows a sectional representation according to FIG. 2, but with the closure cap removed and resultant displacement of the dosing chamber into the ready-to-remove position.

In the ready-to-empty position according to FIG. 4, the dosing chamber 26 is in the active region of the central suction air stream S. An air passage 46 connecting with the suction air channel 12 and formed in the cup wall 40 of the rotary part 22 is associated with the dosing chamber 26. The air passage comprises radial bores which extend in the vicinity of the base of the cup-shaped rotary part 22 with an axial spacing above the upper side of the top 23.

Such an air passage 46 is provided upstream and at a radial spacing from both open ends of the dosing chamber 26. One precaution in this connection is that associated with the end of the dosing chamber 26 which is of larger clear diameter and is formed by a conical transverse bore is an air passage 40 of a smaller diameter than the larger-diameter end and associated with the end of the dosing chamber 26 which is of smaller clear diameter is an air passage 46 of a larger diameter than the smaller-diameter end. This way there is produced a greater reduced pressure with a predominant discharging effect with respect to the administered portion 10' downstream of the air passage 46 of smaller diameter. Nevertheless, the discharge, i.e. emptying of the dosing chamber 26, takes place from both ends. A solution in which the air passages 46 are of the same diameter is shown in the drawings.

The air passages 46, formed on the cup-shaped rotary part 22 guiding the plunger slide 25, are also in flow communication with air inlets 48 spaced radially by way of a rearward annular inflow space 47. The air inlets are also configured as bores and represent the connection to the atmosphere. The annular inflow space 47 is fashioned between the outer side of the cup wall 40 of the cup-shaped rotary part 22 and the inner side of the lateral wall 34 of the mouthpiece 3, as an axial extension of the annular space 41 described. A stepped, radially outwardly protruding sealing collar 49 at the end facing toward the cup opening of the dispersing part 37 serves for separating the annular spaces from one another and for the radial alignment of the dispersing part 37 while supported on the inner side of the lateral wall 34. The sealing collars 49 and 45 of the dispersing part 37 prevent a flow bypass between the air inlets 48 and the annular outlet space 44 in the region of the mouthpiece 3.

The air passages 46 are disposed axially offset in relation to the air inlets 48, the latter lying closer to the mouthpiece 3. The described spatial distancing leads to an initially contra-acting inflow of sucked-in air following on from the main suction air stream S.

The guiding opening 24 for the plunger slide 25 is formed such that it has a wiping-off effect, as a result of which there is also no dosage-falsifying entrainment of powder material that may be sticking to the lateral surface of the plunger slide. The guiding opening 24 is not formed directly by the rotary part 22, but by a sealing bush 50 lining this passage. The sealing bush consists of rubber-elastic material and is held by being clipped into the top 23 by latching means.

Between the rotary part 22 and the housing 2, which forms the storage chamber 11, there is likewise a sealing element. This is achieved by a sealing ring 51 of rubber-elastic material inserted between the inside wall of the storage chamber 11 and the rotary part 22. The sealing ring is fitted under preloading in annular grooves of both parts 2, 22. Both of the peripheral annular grooves, which accommodate the sealing ring 51, have a half-round cross-sectional configuration. The corresponding regions of the sealing ring 51 are correspondingly shaped.

The sealing bush 50 is connected to the rotary part 22 in a rotationally fixed manner. The guiding opening 24 is formed in a manner adapted to the cross-sectional configuration of the plunger slide 25, likewise in an elongate rectangular fashion, and as a result of this positive engagement the plunger slide 25 is also connected to the rotary part 22 in a rotationally fixed manner.

Interacting with the plunger slide 25 is a closure plunger 52, which is movable in relation to the latter outside the storage chamber 11. The closure plunger may consist of a rubber-elastic material and is passed through centrally by the flat portion of the plunger slide 25, for which purpose the closure plunger 52 has a matched bearing opening 53, of an elongate rectangular form in outline. This bearing opening 53 is slightly enlarged with respect to the cross-sectional dimension of the flat portion of the plunger slide 25, as a result of which a low-friction displacement of the closure plug 52 on the plunger slide 25 is achieved.

The closure plunger 52 is provided with a radially outward peripheral sealing lip 54, which in a ready-to-transfer position according to the illustration in FIG. 4 interacts with the inside wall of the cup wall 40 of the rotary part, this being above the air passages 46 with reference to the storage chamber 11.

In this ready-to-transfer position, the closure plug 52 is located in a blocking manner in the suction air channel 12, with the dosing chamber 26 that is provided with the portion 10' of the substance 10 being sealed off on both sides. If the inhaler 1 is put down after it has been activated, that is to say after the plunger 25 slide with the filled dosing chamber 26 has been displaced into the ready-to-transfer position, this does not lead to loss of the apportioned amount from the dosing chamber 26 as a result of the way in which the closure plunger 52 is disposed. The closure plug 52 is fashioned in a self-locking manner.

The displacement of the closure plunger 52 is only possible deliberately, most easily by activation of the suction air stream S, that is to say by the customary intake of inhalation. Depending on the reduced suction pressure that this produces, the closure plunger 52 is displaced axially upward along the portion comprising the flat part of the plunger slide 25, to release the dosing chamber 26 on both sides. The closure plunger 52 is hereby moved into the radially widened overflow region 42, this axial displacement being stop-limited. Serving for this purpose are axially aligned stop webs 55, which extend radially inward from the inside wall of the cup wall 39 of the dispersing part and against which the annular sealing lip 54 of the closure plunger 52 butts in a blocking manner. The radial spacing of the stop webs 55 from one another corresponds to the guiding cross-section of the dispersing part 37 and consequently to the outside diameter of the radial collar 29 on the plunger slide side.

Figure 5:
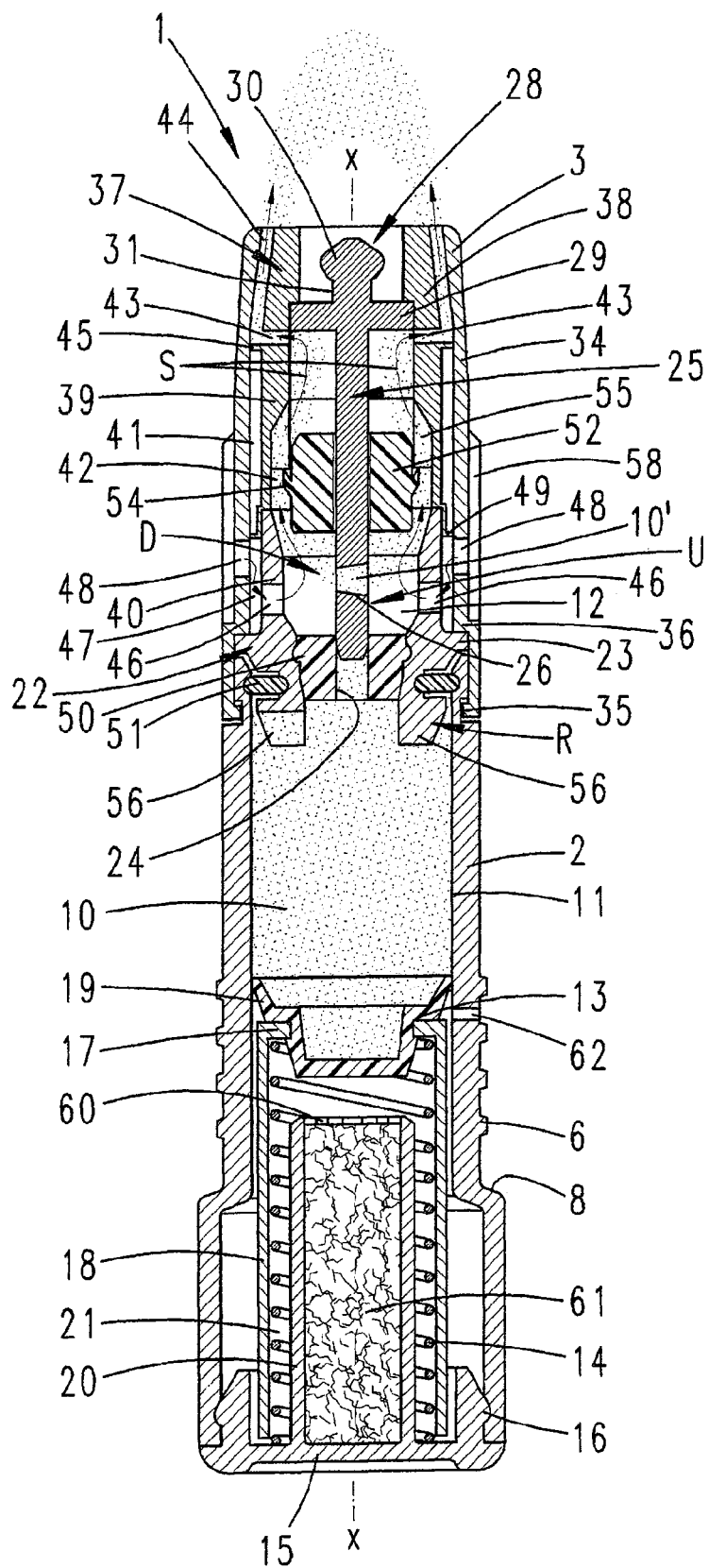
FIG. 5 shows a sectional representation corresponding to FIG. 4, but representing a position in the course of inhalation.

In the course of the inhalation as schematically represented in FIG. 5 flow passes around the closure plunger 52, lying in the region 42 of the mouthpiece 3

Conducive to the emptying of the storage chamber 11 is the way in which the powdered substance 10 is kept ready in the drawing region. Conditions are created to ensure an isostructural or homogeneous filling of the dosing chamber 26, fed from a surrounding region where the substance has been loosened. The rotary part 22 is used in particular for this purpose. It has a rotor R acting in the upper region of the storage chamber 11. Using the rotation of the rotary part 22, a loosening of the stored substance is obtained. Rotor blades 56 form a scoop. In this respect, two rotor blades 56 may be provided, disposed diametrically opposite with respect to the longitudinal center axis x-x of the inhaler 1. The freely extending rotor blades 56 protruding from the base or the top 23 of the rotary part 22 on the storage chamber side are positioned diametrically opposite in such a way that they are sufficiently spaced apart in the circumferential direction. Geometrically, they may substantially take up a quarter sector of the circular cross-section of the storage chamber 11.

In interaction with the plunger slide 25 fashioned as a flat part, the way in which the rotor blades 56 are disposed always achieves a surrounding region where the substance has been loosened. Furthermore, the way in which the dosing chamber 26 is disposed eccentrically in relation to the axis of rotation of the plunger slide 25 achieves optimum filling of the same by means of plunging helically through the mass of substance.

The co-rotation between the mouthpiece 3 and the closure cap 4, lifting off by an unscrewing action, takes place by a claw coupling 57 between the two. This comprises a longitudinal toothing 58 on the lateral wall 34 of the mouthpiece 3, which longitudinal toothing 58 engages in corresponding tooth gaps 59 on the inner side of the closure cap 4.

As the closure cap 4 is lifted off by an unscrewing action, the claw coupling 57 causes a co-rotation of the rotary part 22 and of the parts entrained by it, such as the sealing bush 50, the closure plug 52 and 25 the plunger slide 25, an axial displacement of the plunger slide, brought about by the screw-effected lifting-off displacement of the closure cap 4, being in addition effected by the docking point 28, this axial displacement bringing about a screw-thread-like displacement of the dosing chamber 26 to the transfer point U, that is to say into the ready-to-transfer position according to the illustration in FIG. 4. In the course of the linear displacement of the plunger slide 25, the closure plug 52 remains in its sealing position, supporting itself on the top 23 of the rotary part 22.

The standing spigot 20 rooted at the base 15 of the housing 2 is closed at the end by a screen-like cover 60. In the delimited space created as a result, a moisture-absorbing material 61 is held.

The plunger slide 25 can be varied with respect to the volume of its dosing chamber 26. All that is necessary for this is to exchange the key component of the dosing device D, that is the plunger slide 25, to achieve a different, precisely reproducible dosing of portions 10

The pressure-exerting base 13, acting in the manner of a plunger, is not impaired in its ability to move with respect to the cylinder space, which is provided by the central portion of the housing 2, since there the housing has an air-equalizing opening 62 lying to the rear of the annular lip 19.

The cup-shaped pressure-exerting base 13 has a central indentation, directed away from the storage chamber 11. It is of such a depth on the inside that the end portion of the plunger slide 25 projecting axially downward beyond the rotor blades 56 in the basic position is accommodated in it.

All features disclosed are (in themselves) pertinent to the invention. The disclosure content of the associated/accompanying priority documents (copy of the prior patent application) is also hereby incorporated in full in the disclosure of the application, including for the purpose of incorporating features of these documents in claims of the present application.

The invention claimed is:

1. An inhaler for powdery substances, comprising:
    a mouthpiece and a suction air channel leading to said mouthpiece;
    a storage chamber for storing therein the powdery substance;
    a dipping plunger comprising a movable dosing chamber configured to repeatedly dip the dosing chamber into and out of the storage chamber,
    the movable dosing chamber being provided for apportioning a specific amount of substance from said storage chamber and moving an amount of substance into a ready position for transferring the amount of substance to a user produced suction air stream;
    a closure slide element disposed to close off said dosing chamber in the ready position, wherein the closure slide element is movable relative to the dipping plunger and relative to the mouthpiece into a dose-release position upon application of the user produced airstream.

2. The inhaler according to claim 1, wherein the closure slide element seals off at least one side of the movable dosing chamber in the ready position.

3. The inhaler according to claim 2, wherein the closure slide element seals off a first and a second side of the movable dosing chamber in the ready position.

4. The inhaler according to claim 2, wherein the closure slide element does not seal off a first and a second side of the movable dosing chamber when the closure slide element resides in the dose-release position.

5. The inhaler according to claim 1, wherein said suction air channel is formed with a radially outward direction change above said movable dosing chamber.

6. The inhaler according to claim 1, wherein said dipping plunger comprises a flat plunger.

7. The inhaler according to claim 1 wherein said movable dosing chamber is rotationally movable in a superposed manner and is disposed eccentrically to a rotational axis.

8. The inhaler according to claim 1, wherein said dipping plunger is formed with a radially extending collar forming a part of a flow-deflector.

9. The inhaler according to claim 1, wherein a larger end of said dosing chamber having a larger open diameter is associated with an air passage of a smaller diameter than said larger end of said dosing chamber, and a smaller end of said dosing chamber having a smaller open diameter is associated with an air passage of a larger diameter than said smaller end.

10. The inhaler according to claim 1, which comprises a cup-shaped rotary part having air passages formed therein and guiding said dipping plunger, and wherein said air passages are in fluid communication with air inlets in a lateral wall of said mouthpiece.

11. The inhaler according to claim 10, wherein said air passages are axially displaced with respect to said air inlets, and said air inlets are closer to said mouthpiece.

12. The inhaler according to claim 10, wherein a cup-shaped bottom of said rotary part forms a cover for said storage chamber, and a center of said cup-shaped bottom is formed with a guide opening for said dipping plunger.

13. The inhaler according to claim 10, further comprising a sealing ring encompassing a guide opening in said rotary part and said dipping plunger.

14. The inhaler according to claim 10, further comprising a compressible sealing ring inserted under prestressing between an interior wall of said storage chamber and said rotary part.

15. The inhaler according to claim 1, further comprising a screw cap forming a closure cap cooperating with said mouthpiece via rotational engagement.

* * * * *

UNITED STATES PATENT AND TRADEMARK OFFICE
CERTIFICATE OF CORRECTION

PATENT NO. : 8,701,660 B2  
APPLICATION NO. : 12/062225  
DATED : April 22, 2014  
INVENTOR(S) : Alfred von Schuckmann Page 1 of 1

It is certified that error appears in the above-identified patent and that said Letters Patent is hereby corrected as shown below:

On the title page, at item [73], Assignee, please delete "Siegfried Generics International, Zofingen (CH)" and replace with -- SANOFI SA, Meyrin (CH) --.

Signed and Sealed this  
Second Day of February, 2016

Michelle K. Lee  
*Director of the United States Patent and Trademark Office*